United States Patent
Rudnicki et al.

(10) Patent No.: US 8,361,960 B2
(45) Date of Patent: Jan. 29, 2013

(54) PERIOSTIN-INDUCED PANCREATIC REGENERATION

(75) Inventors: Michael Rudnicki, Ottawa (CA); Johnathan Smid, Gloucester, CA (US)

(73) Assignee: Ottawa Hospital Research Institute, Ottawa, Ontario (CA)

( * ) Notice: Subject to any disclaimer, the term of this patent is extended or adjusted under 35 U.S.C. 154(b) by 0 days.

(21) Appl. No.: 13/062,648

(22) PCT Filed: Sep. 8, 2009

(86) PCT No.: PCT/CA2009/001220
§ 371 (c)(1),
(2), (4) Date: Mar. 7, 2011

(87) PCT Pub. No.: WO2010/025555
PCT Pub. Date: Mar. 11, 2010

(65) Prior Publication Data
US 2011/0172148 A1    Jul. 14, 2011

Related U.S. Application Data

(60) Provisional application No. 61/095,176, filed on Sep. 8, 2008.

(51) Int. Cl.
*A61P 3/10*    (2006.01)
*A61K 38/00*   (2006.01)
(52) U.S. Cl. .............................. 514/7.3; 514/1.1; 514/6.9
(58) Field of Classification Search .................. None
See application file for complete search history.

(56) References Cited

U.S. PATENT DOCUMENTS

| | | | |
|---|---|---|---|
| 4,179,337 | A | 12/1979 | Davis et al. |
| 4,495,285 | A | 1/1985 | Shimizu et al. |
| 4,609,546 | A | 9/1986 | Hiratani |
| 4,766,106 | A | 8/1988 | Katre et al. |
| 6,114,307 | A | 9/2000 | Jaspers et al. |
| 6,709,855 | B1 * | 3/2004 | Stanton et al. ............. 435/283.1 |
| RE39,299 | E | 9/2006 | Vinik et al. |

FOREIGN PATENT DOCUMENTS

| | | | |
|---|---|---|---|
| WO | WO 2005/019471 | * | 3/2005 |
| WO | 2006096565 A2 | | 9/2006 |

OTHER PUBLICATIONS

Kahn et al, Ann Rev. Med. 47: 509-531, 1996.*
Eftychi et al, Diabetes, 53: 870-873, 2004.*
Craven et al., "Overexpression of Cu2+/Zn2+ Superoxide Dismutase Protects Against Early Diabetic Glomerular Injury in Transgenic Mice," Diabetes 50: 2114-2125, 2001.
Erkan et al., "Periostin Creates a Tumor-Supportive Microenvironment in the Pancreas by Sustaining Fibrogenic Stellate Cell Activity," Gastroenterology 132: 1447-1464, 2007.
Goss et al., "Herpes Simplex-Mediated Gene Transfer of Nerve Growth Factor Protects Against Peripheral Neuropathy in Streptozotocin-Induced Diabetes in the Mouse," Diabetes 51: 2227-2232, 2002.
Horiuchi et al., "Identification and Characterization of a Novel Protein, Periostin, with Restricted Expression to Periosteum and Periodontal Ligament and Increased Expression by Transforming Growth Factor Beta," Journal of Bone and Mineral Research, 14(7): 1239-1249, 1999.
Kanno et al., "Periostin, secreted from stromal cells, has biphasic effect on cell migration and correlates with the epithelial to mesenchymal transition of human pancreatic cancer cells," Int. J. Cancer 122: 2707-2718, 2008.
Qian,Y., Genbank Accession No. BQ554374, last updated Dec. 18, 2010.
Strausberg, R., Genbank Accession No. BG242958, last updated Feb. 13, 2001.
Strausberg, R., Genbank Accession No. BG176344, last updated Jan. 12, 2011.
Strausberg, R., Genbank Accession No. BI112981, last updated Jan. 11, 2011.
Takeshita et al., Osteoblast-specific factor 2: cloning of a putative bone adhesion protein with homology with the insect protein fasciclin I, Biochem J. 294: 271-278, 1993.
VanBuren et al., "Assembly, Verification, and Initial Annotation of the NIA Mouse 7.4K cDNA Clone Set," Genome Research 12: 1999-2003, 2002.

* cited by examiner

*Primary Examiner* — Gyan Chandra

(57) ABSTRACT

A method for regenerating pancreatic tissue using recombinant periostin protein, a nucleic acid encoding said periostin and pharmaceutical compositions comprising said periostin are disclosed. Isolation of a nucleic acid encoding a periostin isoform, panc, is also taught.

17 Claims, 10 Drawing Sheets

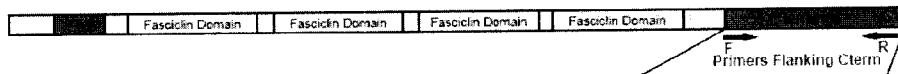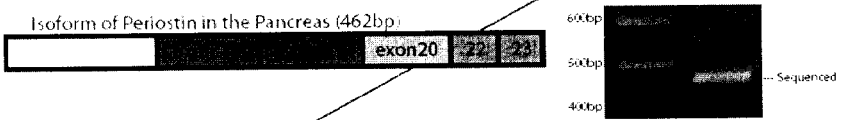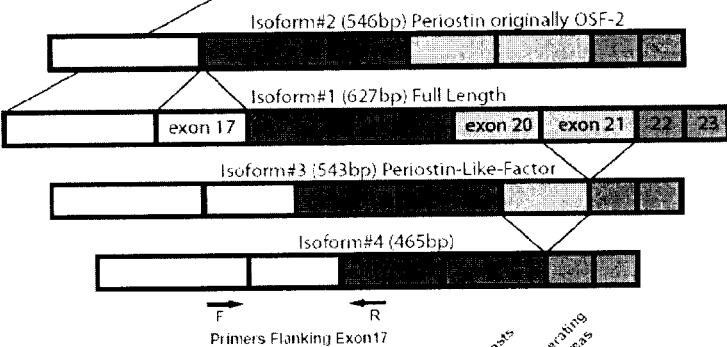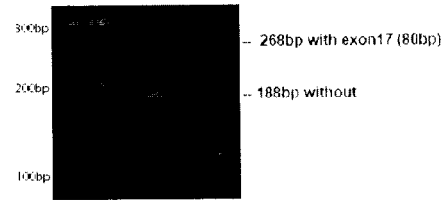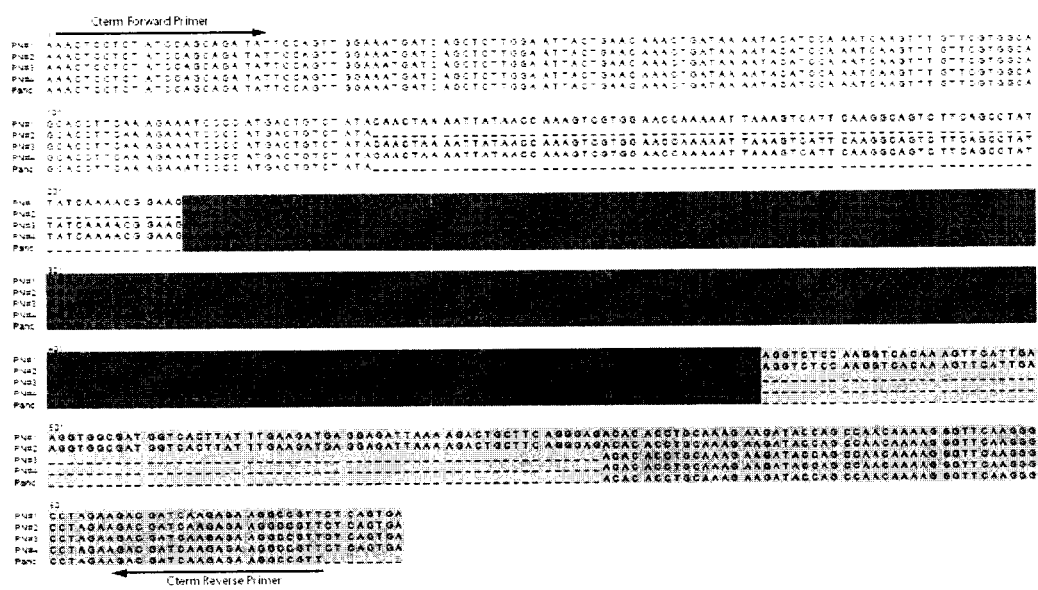
Figure 1

```
         1                                                          50
PN1   AAACTCCTCT ATCCAGCAGA TATTCCAGTT GGAAATGATC AGCTCTTGGA
PN2   AAACTCCTCT ATCCAGCAGA TATTCCAGTT GGAAATGATC AGCTCTTGGA
PN3   AAACTCCTCT ATCCAGCAGA TATTCCAGTT GGAAATGATC AGCTCTTGGA
PN4   AAACTCCTCT ATCCAGCAGA TATTCCAGTT GGAAATGATC AGCTCTTGGA
panc  AAACTCCTCT ATCCAGCAGA TATTCCAGTT GGAAATGATC AGCTCTTGGA 51                                                         100
PN1   ATTACTGAAC AAACTGATAA AATACATCCA AATCAAGTTT GTTCGTGGCA
PN2   ATTACTGAAC AAACTGATAA AATACATCCA AATCAAGTTT GTTCGTGGCA
PN3   ATTACTGAAC AAACTGATAA AATACATCCA AATCAAGTTT GTTCGTGGCA
PN4   ATTACTGAAC AAACTGATAA AATACATCCA AATCAAGTTT GTTCGTGGCA
panc  ATTACTGAAC AAACTGATAA AATACATCCA AATCAAGTTT GTTCGTGGCA 101                                                        150
PN1   GCACCTTCAA AGAAATCCCC ATGACTGTCT ATACAACTAA AATTATAACC
PN2   GCACCTTCAA AGAAATCCCC ATGACTGTCT ATA....... ..........
PN3   GCACCTTCAA AGAAATCCCC ATGACTGTCT ATACAACTAA AATTATAACC
PN4   GCACCTTCAA AGAAATCCCC ATGACTGTCT ATACAACTAA AATTATAACC
panc  GCACCTTCAA AGAAATCCCC ATGACTGTCT ATA....... ..........

151                                                        200
PN1   AAAGTCGTGG AACCAAAAAT TAAAGTCATT CAAGGCAGTC TTCAGCCTAT
PN2   .......... .......... .......... .......... ..........
PN3   AAAGTCGTGG AACCAAAAAT TAAAGTCATT CAAGGCAGTC TTCAGCCTAT
PN4   AAAGTCGTGG AACCAAAAAT TAAAGTCATT CAAGGCAGTC TTCAGCCTAT
panc  .......... .......... .......... .......... ..........

201                                                        250
PN1   TATCAAAACG GAAGGACCTG CAATGACGAA GATCCAAATT GAAGGTGATC
PN2   .......... ....GACCTG CAATGACGAA GATCCAAATT GAAGGTGATC
PN3   TATCAAAACG GAAGGACCTG CAATGACGAA GATCCAAATT GAAGGTGATC
PN4   TATCAAAACG GAAGGACCTG CAATGACGAA GATCCAAATT GAAGGTGATC
```

Figure 2

```
panc   ..........  ....GACCTG  CAATGACGAA  GATCCAAATT  GAAGGTGATC 251                                                    300
PN1    CCGACTTCAG  GCTGATTAAA  GAAGGCGAAA  CGGTGACAGA  AGTGATCCAC
PN2    CCGACTTCAG  GCTGATTAAA  GAAGGCGAAA  CGGTGACAGA  AGTGATCCAC
PN3    CCGACTTCAG  GCTGATTAAA  GAAGGCGAAA  CGGTGACAGA  AGTGATCCAC
PN4    CCGACTTCAG  GCTGATTAAA  GAAGGCGAAA  CGGTGACAGA  AGTGATCCAC
panc   CCGACTTCAG  GCTGATTAAA  GAAGGCGAAA  CGGTGACAGA  AGTGATCCAC 301                                                    350
PN1    GGAGAGCCAG  TCATTAAAAA  GTACACCAAA  ATCATAGATG  GAGTTCCTGT
PN2    GGAGAGCCAG  TCATTAAAAA  GTACACCAAA  ATCATAGATG  GAGTTCCTGT
PN3    GGAGAGCCAG  TCATTAAAAA  GTACACCAAA  ATCATAGATG  GAGTTCCTGT
PN4    GGAGAGCCAG  TCATTAAAAA  GTACACCAAA  ATCATAGATG  GAGTTCCTGT
panc   GGAGAGCCAG  TCATTAAAAA  GTACACCAAA  ATCATAGATG  GAGTTCCTGT 351                                                    400
PN1    TGAAATAACT  GAAAAACAGA  CTCGGGAAGA  ACGAATCATT  ACAGGTCCTG
PN2    TGAAATAACT  GAAAAACAGA  CTCGGGAAGA  ACGAATCATT  ACAGGTCCTG
PN3    TGAAATAACT  GAAAAACAGA  CTCGGGAAGA  ACGAATCATT  ACAGGTCCTG
PN4    TGAAATAACT  GAAAAACAGA  CTCGGGAAGA  ACGAATCATT  ACAG......
panc   TGAAATAACT  GAAAAACAGA  CTCGGGAAGA  ACGAATCATT  ACAGGTCCTG 401                                                    450
PN1    AGATAAAATA  TACCAGGATT  TCCACAGGAG  GTGGAGAAAC  AGGAGAGACC
PN2    AGATAAAATA  TACCAGGATT  TCCACAGGAG  GTGGAGAAAC  AGGAGAGACC
PN3    AGATAAAATA  TACCAGGATT  TCCACAGGAG  GTGGAGAAAC  AGGAGAGACC
PN4    ..........  ..........  ..........  ..........  ..........
panc   AGATAAAATA  TACCAGGATT  TCCACAGGAG  GTGGAGAAAC  AGGAGAGACC 451                                                    500
PN1    TTGCAGAAAT  TCTTGCAAAA  AGAGGTCTCC  AAGGTCACAA  AGTTCATTGA
PN2    TTGCAGAAAT  TCTTGCAAAA  AGAGGTCTCC  AAGGTCACAA  AGTTCATTGA
```

Figure 2 (Continued)

```
PN3   TTGCAGAAAT TCTTGCAAAA AG........ .......... ..........
PN4   .......... .......... .......... .......... ..........
panc  TTGCAGAAAT TCTTGCAAAA AG........ .......... ..........

501                                                  550
PN1   AGGTGGCGAT GGTCACTTAT TTGAAGATGA GGAGATTAAA AGACTGCTTC
PN2   AGGTGGCGAT GGTCACTTAT TTGAAGATGA GGAGATTAAA AGACTGCTTC
PN3   .......... .......... .......... .......... ..........
PN4   .......... .......... .......... .......... ..........
panc  .......... .......... .......... .......... ..........

551                                                  600
PN1   AGGGAGACAC ACCTGCAAAG AAGATACCAG CCAACAAAAG GGTTCAAGGG
PN2   AGGGAGACAC ACCTGCAAAG AAGATACCAG CCAACAAAAG GGTTCAAGGG
PN3   ......ACAC ACCTGCAAAG AAGATACCAG CCAACAAAAG GGTTCAAGGG
PN4   ......ACAC ACCTGCAAAG AAGATACCAG CCAACAAAAG GGTTCAAGGG
panc  ......ACAC ACCTGCAAAG AAGATACCAG CCAACAAAAG GGTTCAAGGG 601                          636
PN1   CCTAGAAGAC GATCAAGAGA AGGCCGTTCT CAGTGA
PN2   CCTAGAAGAC GATCAAGAGA AGGCCGTTCT CAGTGA
PN3   CCTAGAAGAC GATCAAGAGA AGGCCGTTCT CAGTGA
PN4   CCTAGAAGAC GATCAAGAGA AGGCCGTTCT CAGTGA
panc  CCTAGAAGAC GATCAAGAGA AGGCCGTT.. ......
```

Figure 2 (Continued)

```
MGHHHHHHHH HHSSGHIEGR HMRNNHYDKI LAHSRIRGRD QGPNVCALQQ ILGTKKKYFS TCKNWYKKSI
CGQKTTVLYE CCPGYMRMEG MKGCPAVLPI DHVYGTLGIV GATTQRYSD  ASKLREEIEG KGSFTYFAPS
NEAWDNLDSD IRRGLESNVN VELLNALHSH MINKRMLTKD LKNGMIIPSM YNNLGLFINH YPNGVTVNC
ARIIHGNQIA TNGVVHVIDR VLTQIGTSIQ DFIEAEDDLS SFRAAAITSD ILEALGRDGH FTLFAPTNEA
FEKLPRGVLE RFMGDKVASE ALMKYHILNT LQCSESIMGG AVFETLEGNT IEIGCDGDSI TVNGIKMVNK
KDIVTNNGVI HLIDQVLIPD SAKQVIELAG KQQTTFTDLV AQLGLASALR PDGEYTLLAP VNNAFSDDTL
SMVQRLLKLI LQNHILKVKV GLNELYNGQI LETIGGKQLR VFVYRTAVCI ENSCMEKGSK QGRNGAIHIF
REIIKPAEKS LHEKLKQDKR FSTFLSLLEA ADLKELLTQP GDWTLFVPTN DAFKGMTSEE KEILIRDKNA
LQNIILYHLT PGVFIGKGFE PGVTNILKTT QGSKIFLKEV NDTLLVNELK SKESDIMTTN GVIHVVDKLL
YPADTPVGND QLLEIINKLI KYIQIKFVRG STFKEIPVTV Y
```

Figure 3

```
ATGGTTCCTCTCCTGCCCTTATATGCTCTGCTGCTGCTGTTCCTGTGTGATATTAACCCTGCAAATGCCAACAGTTACTA
TGACAAGGTCCTGGCTCACAGCCGCATCAGGGGTCGGGATCAGGGCCCAAACGTCTGTGCCCTCCAGCAAATTCTGGGCA
CCAAAAAGAAATACTTCAGCTCCTGTAAGAACTGGTATCAAGGTGCTATCTGCGGGAAGAAAACCACTGTGCTATATGAA
TGCTGCCCTGGCTATATGAGAATGGAAGGGATGAAAGGCTGCCCCGCAGTGATGCCTATTGACCATGTTTATGGCACGCT
GGGCATTGTGGGAGCCACTACCACTCAGCACTACTCCGATGTCTCGAAGCTGAGAGAAGAGATTGAAGGAAAAGGGTCAT
ACACGTACTTCGCCGAGTAACGAGGCTTGGGAGAACCTGGATTCTGACATTCGCAGAGGACTGGAGAACAATGTCAAT
GTTGAGCTACTGAATGCCTTACACAGCCACATGGTTAATAAGAGAATGTTAACCAAGGACCTGAAACACGGCATGGTTAT
TCCTTCAATGTACAACAATCTGGGGCTTTTTATTAACCATTATCCCAATGGGGTTGTCACTGTGAACTGTGCTCGAGTCA
TCCATGGAACCAGATTGCCACAAATGGTGTCGTCCATGTCATTGACCGTGTCCTGACACAAATTGGTACCTCCATCCAA
GACTTCCTTGAAGCAGAAGACGACCTTTCATCATTTAGAGCAGCCGCCATCACCTCTGACCTCTTGGAGTCCCTTGGAAG
AGATGGTCACTTCACGCTCTTTGCTCCCACCAATGAAGCTTTCGAGAAACTGCCACGAGGTGTCCTAGAAAGGATCATGG
GAGACAAAGTGGCTTCTGAAGCTCTCATGAAGTACCACATCCTAAATACCCTCCAGTGCTCTGAGGCCATCACTGGAGGA
GCCGTGTTTGAGACCATGGAAGGAAACACTATTGAGATAGGGTGCGAAGGGGACAGTATCTCCATTAACGGAATCAAGAT
GGTGAACAAGAAAGACATTGTGACTAAGAATGGTGTCATCCACCTGATTGATGAAGTCCTCATTCCTGATTCTGCCAAAC
AAGTTATTGAGCTGGCTGGAAAACAGCAAACCACTTTCACCGACCTGGTAGCCCAATTAGGCTTGGCATCCTCTCTGAAG
CCAGATGGAGAGTACACCTTATTAGCACCTGTGAACAATGCGTTCTCTGATGACACTCTGAGCATGGACCAACGCCTTCT
TAAGCTAATTCTGCAAAATCACATATTGAAAGTAAAAGTTGGCCTTAGCGACCTCTACAATGGACAGATACTGGAAACCA
TTGGAGGCAAACAACTCCGAGTCTTTGTGTATCGGACGGCTATCTGCATAGAAAACTCATGCATGGTGAGAGGAAGCAAG
CAGGGAAGGAATGGTGCCATTCACATATTCCGAGAAATCATCCAACCAGCAGAGAAATCCCTGCACGACAAGCTGCGGCA
AGACAAGCGCTTTAGCATCTTCCTCAGCCTCCTTGAAGCTGCAGATTTGAAAGATCTCCTGACACAGCCCGGAGATTGGA
CCTTGTTTGCACCAACCAATGATGCCTTCAAGGGAATGACTAGCGAAGAAAGGGAGCTTCTGATTGGGGATAAAAATGCT
CTCCAAAACATCATTCTTTATCACCTGACCCCAGGGGTTTATATTGGAAAGGGATTCGAACCCGGAGTCACTAATATCCT
GAAGACCACACAGGGAAGCAAAATCTATCTGAAAGGAGTAAACGAAACGCTTCTAGTGAATGAGTTGAAGTCCAAAGAAT
CTGACATCATGACGACAAATGGTGTCATCCACGTCGTGGACAAACTCCTCTATCCAGCAGATATTCCAGTTGGAAATGAT
CAGCTCTTGGAATTACTGAACAAACTGATAAAATACATCCAAATCAAGTTTGTTCGTGGCAGCACCTTCAAAGAAATCCC
CATGACTGTCTATAGACCTGCAATGACGAAGATCCAAATTGAAGGTGATCCCGACTTCAGGCTGATTAAAGAAGGCGAAA
CGGTGACAGAAGTGATCCACGGAGAGCCAGTCATTAAAAAGTACACCAAAATCATAGATGGAGTTCCTGTTGAAATAACT
GAAAAACAGACTCGGGAAGAACGAATCATTACAGGTCCTGAGATAAAATATACCAGGATTTCCACAGGAGGTGGAGAAAC
AGGAGAGACCTTGCAGAAATTCTTGCAAAAAGACACACCTGCAAAGAAGATACCAGCCAACAAAAGGGTTCAA
GGGCCTAGAAGACGATCAAGAGAAGGCCGTTCTCAGTGA
```

Figure 5A

```
MVPLLPLYALLLLFLCDINPANANSYYDKVLAHSRIRGRDQGPNVCALQQILGTKKKYFSSCKNWYQGAI
CGKKTTVLYECCPGYMRMEGMKGCPAVMPIDHVYGTLGIVGATTTQHYSDVSKLREEIEGKGSYTYFAPS
NEAWENLDSDIRRGLENNVNVELLNALHSHMVNKRMLTKDLKHGMVIPSMYNNLGLFINHYPNGVVTVNC
ARVIHGNQIATNGVVHVIDRVLTQIGTSIQDFLEAEDDLSSFRAAAITSDLLESLGRDGHFTLFAPTNEA
FEKLPRGVLERIMGDKVASEALMKYHILNTLQCSEAITGGAVFETMEGNTIEIGCEGDSISINGIKMVNK
KDIVTKNGVIHLIDEVLIPDSAKQVIELAGKQQTTFTDLVAQLGLASSLKPDGEYTLLAPVNNAFSDDTL
SMDQRLLKLILQNHILKVKVGLSDLYNGQILETIGGKQLRVFVYRTAICIENSCMVRGSKQGRNGAIHIF
REIIQPAEKSLHDKLRQDKRFSIFLSLLEAADLKDLLTQPGDWTLFAPTNDAFKGMTSEERELLIGDKNA
LQNIILYHLTPGVYIGKGFEPGVTNILKTTQGSKIYLKGVNETLLVNELKSKESDIMTTNGVIHVVDKLL
YPADIPVGNDQLLELLNKLIKYIQIKFVRGSTFKEIPMTVYRPAMTKIQIEGDPDFRLIKEGETVTEVIH
GEPVIKKYTKIIDGVPVEITEKQTREERIITGPEIKYTRISTGGGETGETLQKFLQKDTPAKKIPANKRV
QGPRRRSREGRSQ*
```

Figure 5B

PERIOSTIN-INDUCED PANCREATIC REGENERATION

REFERENCE TO SEQUENCE LISTING SUBMITTED ELECTRONICALLY VIA EFS-WEB

The content of the electronically submitted sequence listing (Name: 3100_0010001_Sequence_Listing.txt; Size: 20,737 bytes; and Date of Creation: Feb. 6, 2012) filed with the application is incorporated herein by reference in its entirety.

CROSS REFERENCE TO RELATED APPLICATIONS

This application is a U.S. national phase application of International Application No. PCT/CA2009/001220, filed Sep. 8, 2009; which application claims the benefit of U.S. Provisional Application No. 61/095,176, filed Sep. 8, 2008.

FIELD OF THE INVENTION

The present invention relates generally to the use of periostin for the regeneration of pancreatic tissue.

BACKGROUND OF THE INVENTION

The pancreas produces digestive enzymes, as well as several important hormones, including insulin, glucagon and somatostatin. The hormone producing cells are grouped together in the Islets of Langerhans, which make up approximately 1 to 2% of the pancreas. In a healthy pancreas, insulin is produced by β-cells in the Islets of Langerhans in response to increased levels of blood glucose. There are a number of diseases that result from, or in, the loss of pancreatic tissue. These diseases include diabetes mellitus (both Type 1 and 2) and exocrine pancreatic insufficiency.

Type 1 diabetes (insulin-dependent diabetes mellitus) is an autoimmune disorder in which a body's immune system attacks the β-cells, destroying them or sufficiently damaging them such that little or no insulin is produced. Although insulin replacement therapy, strict diet and careful blood glucose monitoring can limit the complications associated with diabetes, it is desirable to replace or regenerate the pancreas.

Type 2 diabetes (non-insulin-dependent diabetes mellitus) is a metabolic disorder that is initially characterized by insulin resistance, but ultimately characterized by the failure of pancreatic β-cells to match insulin production with insulin demand.

Exocrine pancreatic insufficiency (EPI) is the inability to properly digest food due to a lack of digestive enzymes made by the pancreas. EPI is found in humans afflicted with cystic fibrosis and Shwachman-Diamond Syndrome. It is caused by a progressive loss of the pancreatic cells that make digestive enzymes. Chronic pancreatitis is the most common cause of EPI in humans. Loss of digestive enzymes leads to maldigestion and malabsorption of nutrients.

There is a need in the art to develop methods and medications for regenerating pancreatic tissue.

Surgical transplantation of the islets has not yet proven to be effective, but it is known that pancreatic cells have the ability to regenerate. Pancreas regeneration-promoting factors, such as HIP, INGAP, GLP-1, Exendin-4, have been investigated (e.g. WO 2006/096565, U.S. Pat. No. 6,114,307, and U.S. Pat. No. Re. 39,299).

Periostin is an approximately 90 kDa secreted protein, preferentially expressed in the periosteum in bone tissues. (Takeshita et al. (1993). *Biochem. J.*, 294:271-8; Horiuchi et al. (1999). *J. Bone Miner. Res.*, 14:1239-49). Periostin comprises an $NH_2$-terminal secretory signal peptide, followed by a cysteine-rich domain, four internal homologous repeats, and a COOH-terminal hydrophilic domain. Within each repeat domain, two regions are highly conserved. Periostin has been identified in various cancers and its presence has been proposed as a marker and a therapeutic target for cancer (Kanno et al. (2008) *Int. J. Cancer* 122: 1707-18). Periostin has also been shown to be secreted by pancreatic stellate cells (PSCs) and perpetuate PSC fibrogenic activity while supporting pancreatic tumor cell growth under stress conditions (Erkan, et al. (2007) *Gastroenterology* 132:1447-64).

SUMMARY OF THE INVENTION

In a first aspect, the present invention provides a method for regenerating pancreatic tissue by administering periostin. The regenerated tissue can include β-cells. The method of the invention can be used to treat disease that result from, or in, the loss of pancreatic tissue, such as diabetes Type 1, diabetes Type 2, and EPI.

In another aspect, the administration can be of a nucleotide sequence encoding periostin protein.

In a further aspect, the present invention provides a nucleotide sequence encoding periostin protein, the sequence comprising: sequence panc (FIG. 1); a nucleotide sequence which is homologous to sequence panc; or a nucleotide sequence which hybridizes to the complement of sequence panc.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1A-C shows a schematic of the periostin protein encoded by five different nucleotide sequences.

Fig. 1D shows a nucleotide sequence alignment of five periostin nucleotide sequences which encode the variable portions of isoforms of periostin protein PN1 (SEQ ID NO: 6); PN2 (SEQ ID NO: 7); PN3 (SEQ ID NO: 8); PN4 (SEQ ID NO: 9); panc (SEQ ID NO: 1), illustrated in FIG. 1A-C.

FIG. 2 shows another view of FIG. 1D listing PN1 (SEQ ID NO: 6) PN2 (SEQ ID NO: 7); PN3 (SEQ ID NO: 8); PN4 (SEQ ID NO: 9); panc (SEQ ID NO: 1).

FIG. 3 shows the amino acid sequence of recombinant human periostin protein (SEQ ID NO: 10).

In FIG. 4A, diamonds indicate mouse pairs with normal blood-glucose levels in periostin-treated mice, but STZ-induced diabetes in periostin-untreated mice; triangles indicate mouse pairs with STZ-induced diabetes in both periostin-treated and -untreated mouse pairs.

FIG. 4B shows blood glucose levels (mmol/L) of the mouse pairs from FIG. 4A which were treated with periostin between 40 and 60 μg/kg body weight.

FIG. 5A shows a nucleotide sequence encoding the isoform of periostin protein (SEQ ID NO: 3) illustrated by FIG. 1B.

FIG. 5B shows the amino acid sequence of the isoform of periostin protein (SEQ ID NO: 2) illustrated by FIG. 1B and encoded by the sequence shown in FIG. 5A.

FIGS. 6A and 6C show infiltration of GFP-expressing wild type donor cells 3 days and one week after injection. FIG. 6A is a magnified view of the area indicated by the arrow in FIG. 6B. FIGS. 6D-F show that pancreas injected with mesenchymal cells exhibited: (D) formation of tubular complexes expressing E-Cadherin and Ngn3; (E) GFP-expressing cells surrounding Cytokeratin-7 ductal structures; and (F) GFP-expressing cells did not express Pdx1.

DETAILED DESCRIPTION

Figure 4:
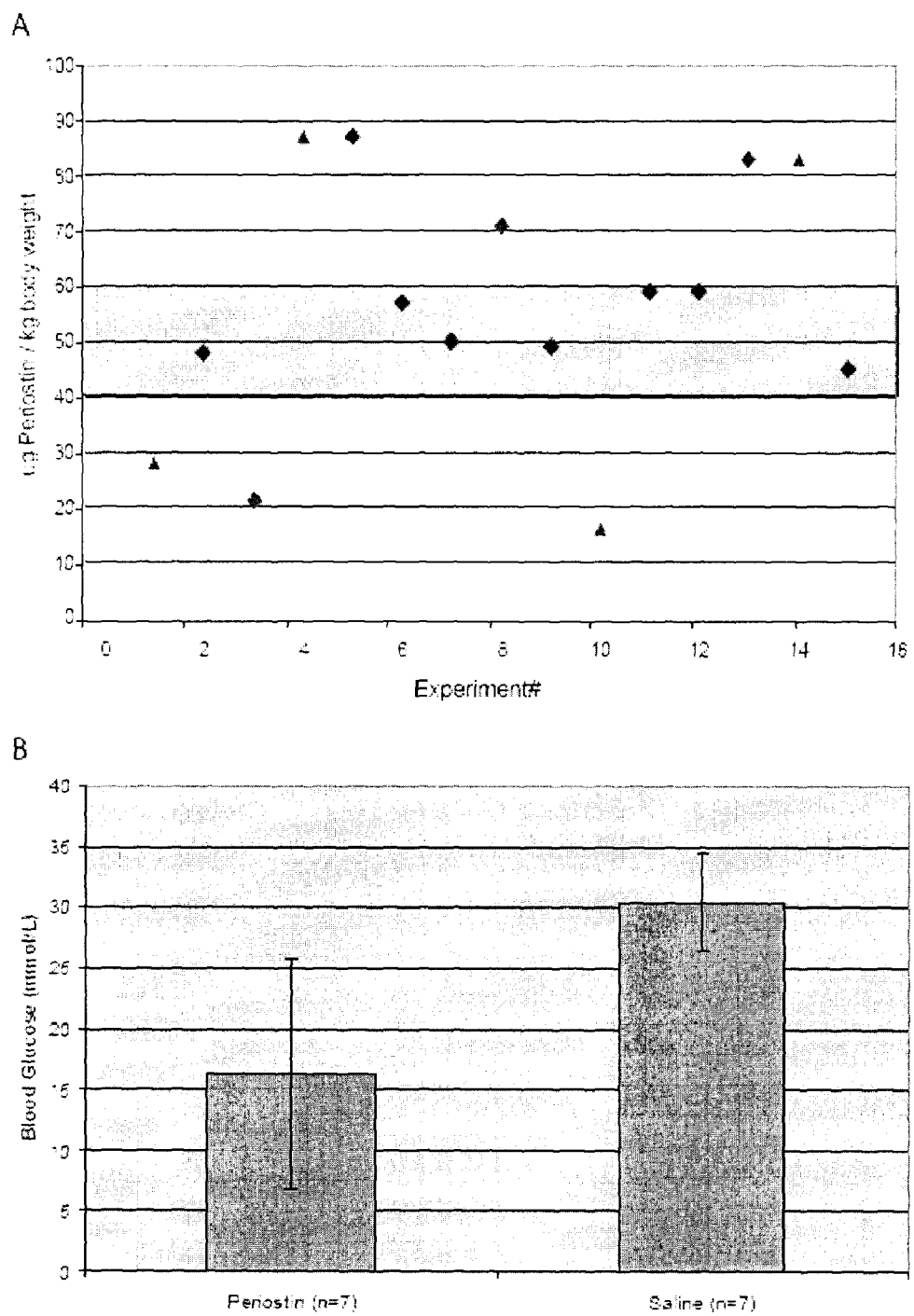
FIG. 4A-B summarizes 15 experiments where paired mice were treated with Streptozotocin and periostin (at varying concentrations), or Streptozotocin alone.

Generally, the present invention provides a method for regenerating pancreatic tissue using periostin. In one particular embodiment, the present invention provides a method for regenerating various pancreatic cells in the Islets of Langerhans using periostin. In a further embodiment, the present invention provides a method for regenerating β-cell cells in the Islets of Langerhans using periostin. In another embodiment, the invention encompasses a novel isoform of periostin, including the nucleic acid encoding the novel isoform.

Periostin exists in various isoforms. As used here, an "isoform" is defined as "any of two or more functionally similar proteins that have a similar but not identical amino acid sequence and are either encoded by different genes or by RNA transcripts from the same gene which have had different exons removed." (Merriam-Webster's Medical Dictionary OnLine)

As shown in FIG. 1, the nucleic acid sequence encoding periostin consists of a conserved EMI domain (a small cysteine-rich module of ~75 amino acids first named after its presence in proteins of the EMILIN family) and four fasciclin repeats. The carboxy terminus comprises a number of exons. Variations in how these exons are spliced out result in various isoforms of periostin.

FIGS. 1 and 2 illustrate four nucleotide sequences encoding four known isoforms of murine periostin. Although these sequences were determined from nucleic acids isolated from mice, it is believed that other mammalian species will contain periostin genes which are substantially similar. Isoform #1 is the longest known isoform of periostin and includes all 23 exons (encoded by nucleotide sequence PN1, FIG. 2). Isoform #2 (encoded by nucleotide sequence PN2, FIG. 2) was the first identified isoform of the periostin protein and originally named Osteoblast Specific Factor-2 (OSF-2); it excludes exon 17. Isoform #3 was more recently named Periostin-Like-Factor (PLF) and includes exon 17 but excludes exon 21 (encoded by nucleotide sequence PN3, FIG. 2). Isoform #4 is currently the shortest published isoform of periostin and excludes exons 20 and 21 (encoded by nucleotide sequence PN4, FIG. 2).

The present invention encompasses a fifth isoform of periostin, which is novel, referred to herein as PANC (the protein being identified by all capital letters). PANC is the most commonly expressed isoform of periostin during pancreatic regeneration. PANC is similar in size to isoform #4, but excludes exons 17 and 21, as shown by direct sequencing. FIG. 1 shows an alignment of the variable portions of the nucleotide sequences encoding PANC (SEQ ID No: 1, FIG. 2) and the above described four murine isoforms of periostin. Thus, the present invention encompasses both the nucleic acid sequence for panc (the DNA being identified by all lower-case letters), and the PANC protein, as well as the isolated panc nucleic acids and PANC proteins.

FIG. 3 shows the amino acid sequence of recombinant human periostin protein. FIG. 5A shows a nucleotide sequence (SEQ ID No: 3) encoding the murine isoform of periostin protein illustrated by FIG. 1B. FIG. 5B shows the amino acid sequence (SEQ ID No: 2) of the murine isoform of periostin protein illustrated by FIG. 1B and which is encoded by the sequence shown in FIG. 5A.

In diabetes type 1, the immune system attacks the pancreas; thus in one aspect the periostin molecules may be administered in combination with immunosuppresants.

Definitions: The term "treat a condition or disease" in the context of the present invention means preventing, arresting the development or retarding the progression of the condition or disease.

The term "regeneration" in the context of the present invention encompasses both increasing the number of cells (proliferation) as well as differentiating stem cells into new cells. Regeneration of pancreatic tissue includes proliferation of new pancreatic cells, induction of stellate cell proliferation, and/or tubular complex formation.

Periostin Nucleic Acid Molecules: The periostin nucleic acid molecules of the invention can be cDNA, genomic DNA, synthetic DNA, or RNA, and can be double-stranded or single-stranded (i.e., either a sense or an antisense strand). Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to coding sequences, e.g., they can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. The nucleic acids can be those of a human, non-human primate (e.g., monkey), mouse, rat, guinea pig, cow, sheep, horse, pig, rabbit, dog, or cat. Combinations or modifications of the nucleotides within these types of nucleic acids are also encompassed.

In addition, the isolated nucleic acid molecules of the invention encompass segments that are not found as such in the natural state. Thus, the invention encompasses recombinant nucleic acid molecules (for example, isolated nucleic acid molecules encoding periostin incorporated into a vector (for example, a plasmid or viral vector) or into the genome of a heterologous cell (or the genome of a homologous cell, at a position other than the natural chromosomal location)).

A periostin family gene or protein can be identified based on its similarity to the relevant periostin gene or protein, respectively. For example, the identification can be based on sequence identity. The invention features isolated nucleic acid molecules which are at least 50% (or 55%, 65%, 75%, 85%, 95%, or 98%) identical to: (a) the nucleotide sequence of panc (FIG. 2); and (b) a nucleic acid molecule which includes a segment of at least 30 (e.g., at least 50, 100, 150, 150, 200, 250, 300, 350, 400, 500, 700, 900, 1100, 1400, 1700, 2000, 2200, 2250, 2300 or 2310) nucleotides of panc (FIG. 2).

The determination of percent identity between two sequences is accomplished using the mathematical algorithm of Karlin and Altschul (1993) Proc. Natl. Acad. Sci. USA 90:5873 5877. Such an algorithm is incorporated into the BLASTN and BLASTP programs of Altschul et al. (1990) J. Mol. Biol. 215, 403 410. BLAST nucleotide searches are performed with the BLASTN program, score=100, wordlength=12, to obtain nucleotide sequences homologous to periostin encoding nucleic acids. BLAST protein searches are performed with the BLASTP program, score=50, wordlength=3, to obtain amino acid sequences homologous to the periostin polypeptide. To obtain gapped alignments for comparative purposes, Gapped BLAST is utilized as described in Altschul et al. (1997) Nucleic Acids Res. 25:3389 3402. When utilizing BLAST and Gapped BLAST programs, the default parameters of the respective programs (e.g., XBLAST and NBLAST) are used.

Hybridization can also be used as a measure of homology between two nucleic acid sequences. A periostin-encoding nucleic acid sequence, or a portion thereof, can be used as a hybridization probe according to standard hybridization techniques. The hybridization of a periostin probe to DNA or RNA from a test source (e.g., a mammalian cell) is an indication of the presence of periostin DNA or RNA in the test source. Hybridization conditions are known to those skilled in the art and can be found in Current Protocols in Molecular Biology, John Wiley & Sons, N.Y., 6.3.1 6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The invention also encompasses: (a) vectors that contain any of the foregoing periostin related coding sequences and/or their complements (that is, "antisense" sequences); (b) expression vectors that contain any of the foregoing periostin related coding sequences operably linked to any transcriptional/translational regulatory elements necessary to direct expression of the coding sequences; (c) expression vectors encoding, in addition to a periostin polypeptide, a sequence unrelated to periostin, such as a reporter, a marker, or a signal peptide fused to periostin; and (d) genetically engineered host cells (see below) that contain any of the foregoing expression vectors and thereby express the nucleic acid molecules of the invention.

Recombinant nucleic acid molecules can contain a sequence encoding periostin or periostin having an heterologous signal sequence. The full length periostin polypeptide, or a fragment thereof, may be fused to such heterologous signal sequences or to additional polypeptides. Similarly, the nucleic acid molecules of the invention can encode the mature form of periostin or a form that includes an exogenous polypeptide that facilitates secretion.

The transcriptional/translational regulatory elements referred to above and further described below include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trt system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neon$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a periostin polypeptide and the second portion being, for example, the reporter described above or an Ig constant region or part of an Ig constant region, e.g., the CH2 and CH3 domains of IgG2a heavy chain. Other hybrids could include an antigenic tag or His tag to facilitate purification.

The expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecule of the invention; insect cell systems infected with recombinant virus expression vectors (for example, baculovirus) containing the nucleic acid molecule of the invention; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a periostin nucleotide sequence; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors of the invention can then be used, for example, for large or small scale in vitro production of a periostin polypeptide or antigenic fragment thereof by methods known in the art. In essence, such methods involve culturing the cells under conditions that maximize production of the polypeptide or antigenic fragment and isolating it from the cells or from the culture medium.

Periostin Protein/Polypeptide: The periostin protein/polypeptides of the invention and for use in the invention include periostin with and without a signal peptide. They also include recombinant forms and isoforms.

The amino acid sequences of the periostin molecules can be identical to the wild-type sequences of the periostin molecules. Polypeptides which are substantially identical to the wild-type sequences of periostin are also encompassed. As applied to proteins, the term "substantial identity" may mean that two sequences, when optimally aligned, such as by the programs GAP or BESTFIT using default gap weights, typically share at least about 70 percent sequence identity, alternatively at least about 80, 85, 90, 95 percent sequence identity or more. Alternatively, any of the polypeptide can contain mutations such as deletions, additions, or substitutions. All that is required is that the mutant periostin molecule have at least 5% (e.g., 10%, 20%, 30%, 40%, 50%, 60%, 70%, 80%, 90%, 95%, 99%, 100%, or even more) of the ability of the wild-type periostin molecule to bind to an antibody specific for wild-type periostin.

For amino acid sequences, amino acid residues that are not identical may differ by conservative amino acid substitutions. The term "conservative substitutions" refers to replacement of an amino acid with another amino acid wherein both amino acids are members of a group of amino acids having certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

The polypeptides can be purified from natural sources (e.g., blood, serum, plasma, tissues or cells such as pancreas, lung, placenta, or colon tissue, or any cell that naturally produces periostin polypeptides, in cancerous or normal cells). The periostin molecules can be those of a human, non-human primate (e.g., a monkey), mouse, rat, guinea pig, cow, sheep, horse, pig, rabbit, dog, or cat. Smaller peptides (less than 100 amino acids long) can also be conveniently synthesized by standard chemical means. In addition, both polypeptides and peptides can be produced by standard in vitro recombinant DNA techniques and in vivo transgenesis using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology [Green Publishing Associates and Wiley Interscience, N.Y., 1989].

Recombinant periostin can be used in the method of the invention. An example of a recombinant periostin useful in the present invention is provided in FIG. 3.

The proteins and polypeptides of the invention can also be produced from any of the nucleic acid molecules discussed above, by techniques known in the art.

The polypeptides of the invention include fragments of full length periostin, wherein such fragments are also able to regenerate pancreatic tissue. Such a polypeptide fragment may contain a sequence of at least 15 (or 30, 50, 100 or 150) consecutive amino acids of a periostin protein. The polypeptide fragment will contain a portion of periostin that is biologically active in the absence of the other portions of the protein. As is known in the art, it is often the case that a relatively small number of amino acids can be removed from either end of a protein without destroying activity.

The polypeptide or polypeptide fragment may be part of a larger protein, such as a genetic fusion with a second protein or polypeptide. Alternatively, the polypeptide or polypeptide fragment may be conjugated to a second protein, for example, by means of a cross-linking agent.

Periostin or polypeptide portions thereof can be chemically modified by covalent conjugation to a polymer. This may be done to increase its circulating half-life, for example. Polymers, and methods to attach them to peptides, are shown in U.S. Pat. Nos. 4,766,106, 4,179,337, 4,495,285, and 4,609,546. Examples of polymers are polyoxyethylated polyols and polyethylene glycol (PEG). PEG is soluble in water at room temperature and has the general formula: $R(O-CH_2-CH_2)_n O-R$ where R can be hydrogen, or a protective group such as an alkyl or alkanol group. The protective group may have between 1 and 8 carbons, and may be methyl. The symbol n is a positive integer, typically between 1 and 1,000, and possibly between 2 and 500. The PEG has a typical average molecular weight between 1000 and 40,000, and may be between 2000 and 20,000, or between 3,000 and 12,000. PEG may have at least one hydroxy group, and may have a terminal hydroxy group.

Pharmaceutical Formulations and Routes of Administration: Pharmaceutical compositions containing a periostin protein or fragments thereof may be used for treatment of pancreatic insufficiency. In another aspect, the pharmaceutical compositions may contain a periostin nucleotide sequence in accordance with the invention.

The compositions of the present invention may be formulated in a conventional manner using one or more pharmaceutically acceptable carriers, such as for oral, buccal, intranasal, parenteral (e.g., intravenous, intramuscular or subcutaneous), topical or rectal administration or in a form suitable for administration by inhalation. The compositions may be injected directly into the pancreas, into circulation, or into intraperitoneal space. The administration can be a surgical insertion of a gel or matrix comprising the composition.

When using a liquid formulation, the polypeptides or nucleic acids may be formulated at different concentrations or using different formulants. For example, these formulants may include oils, polymer; vitamins, carbohydrates, amino acids, salts, buffers, albumin, surfactants, or bulking agents. Carbohydrates include sugar or sugar alcohols such as mono-, di-, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcelloluose, or mixtures thereof. Sucrose is an example. Sugar alcohol is defined as a $C_4$ to $C_8$ hydrocarbon having an —OH group and includes galactitol, inositol, mannitol, xylitol, sorbitol, glycerol, and arabitol. Mannitol is an example. These sugars or sugar alcohols mentioned above may be used individually or in combination. There is no fixed limit to amount used as long as the sugar or sugar alcohol is soluble in the aqueous preparation. The sugar or sugar alcohol concentration is generally between 1.0 w/v % and 7.0 w/v %, and may be between 2.0 and 6.0 w/v %. Amino acids include levorotary (L) forms of carnitine, arginine, and betaine; however, other amino acids may be added. Polymers include polyvinylpyrrolidone (PVP) with an average molecular weight between 2,000 and 3,000, or polyethylene glycol (PEG) with an average molecular weight between 3,000 and 5,000. Often a buffer is used in the composition to minimize pH changes in the solution before lyophilization or after reconstitution, if these are used. Most any physiological buffer may be used, but citrate, phosphate, succinate, and glutamate buffers or mixtures thereof are typical. The concentration may be is from 0.01 to 0.3 molar. Surfactants can also be added to the formulation.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

"Pharmaceutically acceptable excipient", as used herein, means an excipient that is useful in preparing a pharmaceutical composition that is generally safe, non- toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

EXAMPLES

Surgical Procedures. In all surgical procedures, 45 minutes to one hour before the surgery mice are given a dosage of 0.05 mg/kg of diluted Buprenorphine (0.03 mg/ml) subcutaneously. Mice are induced in an anesthetic box with Isoflurane gradually increased to 5%. The anesthetic is delivered by an Ohio Forane vaporizer (induction box) and a Isoflurane vaporizer (mask). Once anesthetized, the mice are transferred to a face mask with Isoflurane at 1.5%. The surgical area is shaved and cleaned with Endure soap, rinsed with sterile water and surgically prepared with Chlorahexseptic solution. BNP eye ointment is placed in the animals eyes to protect them from drying out during the anesthesia. 1 ml of sterile saline is administered subcutaneously prior to surgery. During the surgery, the mice are maintained on Isoflurane at 1.5% (increased or decreased as necessary). Once the surgery is complete the mice are place on oxygen for approximately 1 minute and then returned to their cage as soon as they start to move.

To remove pancreatic tissue access to the abdominal cavity was obtained by performing a midline incision. First, a 1 to 1.5 cm incision was made through the skin in the middle of the abdomen using a No. 10 scalpel blade. Using forceps the skin was gently separated from the abdominal wall to reveal the midline of the abdomen. The midline was lifted with rat tooth forceps and a small cut less than 1 cm was made with scissors through the body wall. Once located the splenic pancreatic lobe was lifted through the incision with forceps. The entire splenic lobe and distal portions of the gastric and duodenal pancreatic lobes were removed by gentle abrasion with forceps and a cotton applicator to ensure no major veins or arteries were broken. If excessive bleeding was observed the site of bleeding was clamped for several minutes to promote clotting. Once removed, only a small portion (~30%) of the pancreas remained along the duodenum. The pancreas that was surgically removed was approximately 70% of the total pancreas, as was confirmed by weighing the removed and remnant portions during a pilot study. The body wall was closed with silk surgical sutures (Johnson&Johnson) in two to three discontinuous sutures. The skin was closed with two to three surgical staples (Fisher). Once the surgery was complete the mice were placed on oxygen for approximately one minute and then returned to their cage as soon as they began to move. Blood glucose levels were analyzed every other day checking blood sugar levels for increased glucose. In addition, mice were given 0.05 mg/kg Buprenorphine subcutaneously every day following surgery for the first week.

Example 1

Pancreatic Regeneration Using Recombinant Periostin

To elucidate the role periostin plays in pancreatic regeneration, a recombinant periostin protein was injected into the pancreas. Recombinant periostin protein, supplied by BioVendor (RD172045100), was re-suspended and diluted in saline at a concentration of 10 ng/µl. The recombinant periostin protein (the 671 amino acid sequence shown in FIG. 3) is human periostin protein truncated at the C-terminus and is representative of the sequence common to all four known isoforms. 10 µl (100 ng or 5 µg/kg) was injected directly into the pancreas. Direct injection was performed by exposing the pancreas with a midline incision, as outlined above, and injecting 10 µl recombinant periostin solution (50 ng/µl) directly into the pancreas with a Hamilton syringe. Vehicle-treated animals received the same amounts of buffer diluted into saline. Following injection into the pancreas the body wall was closed with sutures and the skin with wound clips, as was done following pancreatectomy. Mice were monitored daily and given 0.05 mg/kg Buprenorphine subcutaneously every day following the first week of surgery. Following the surgery BrdU (Sigma) was administered in the drinking water at 0.8 mg/ml to continuously label of dividing cells.

Twenty-four hours after being injected, periostin induced widespread proliferation when compared to a saline injection. Histology shows that this proliferation was outside of islets, ducts and acinar cells and localized to cells expressing vimentin. During regeneration, periostin is localized in the regenerating tip of the pancreas surrounding Cytokeratin7+, and Ecad+ tubular complexes. These complexes are the sources of pancreatic proliferation, as shown by Ki67 immunostaining. Relative to the resting pancreatic periostin mRNA, the periostin mRNA is increased nearly ten fold three days following pancreatectomy. This compares with only a three fold increase during fetal development.

Three days following periostin injection the number of cells expressing vimentin had increased substantially. This increase was localized to areas with tubular complexes, while other areas of the pancreas expressed normal levels of vimentin. However, three days following periostin injection, proliferation no longer occurred within vimentin expressing cells but within Cytokeratin7 expressing tubular complexes. The tubular complexes expressed E-cadherin as did ductal, islet and acinar cells but showed increased proliferation as shown by increased Ki67 immunostaining. The tubular complexes also expressed the pancreatic progenitor markers Pdx-1 and Ngn3. Ngn3+ cells were also found outside of tubular complexes but within close proximity. In distal areas to tubular complex formation Ngn3+ cells were absent.

One week after injection of periostin the stroma was increased as noted by the accumulation of E-cadherin negative cells relative to saline injected pancreata. Although only a few tubular complexes remained in the periostin injected pancreata, proliferation was widespread compared to the saline injected control. However, now proliferation was within E-cadherin expressing cells but not exclusively within tubular complexes. Proliferation was within amylase expressing acinar cells, and absent in the surrounding stroma. The surrounding stroma showed accumulation of BrdU and varied in size from 10 µm to 300 µm in width. The largest accumulations of stroma still contained some E-cadherin positive tubular complexes; however, they were not as abundant as they were at three days following periostin injection. Doses of greater than 500 µg/kg of body weight for mice, resulted in increased pancreatic cell death, particularly within amylase secreting exocrine cells.

Example 2

Pancreatic Regeneration Using Intra Peritoneal Injection

To determine if periostin could be administered in a less invasive approach but still induce pancreatic regeneration, the recombinant protein (BioVendor; RD172045100) was injected via an intra peritoneal injection at 50 µg/kg of body weight, as opposed to being directly injected into the pancreas. One week following periostin injection, an increase in BrdU uptake by islet cells appeared relative to saline injected controls. In addition, there was increased proliferation within islets, as shown by Ki67 staining compared to saline injected controls. About a two-fold increase (n=3) in the number of insulin-secreting β-cells was observed using FACS analysis of MIP-GFP mice that were injected with periostin or saline. Comparing periostin injected mice with littermate saline injected controls showed a more than two-fold increase in the number of β cells.

Example 3

Pancreatic Regeneration in STZ-Induced Diabetes Using Recombinant Periostin

Streptozotocin (STZ) selectively targets and destroys pancreatic β-cells in mammals. It may be used to produce an animal model for Type 1 diabetes. In order to induce diabetes in mice, 100 mg/kg of STZ was intraperitoneal injected every other day until the mouse became diabetic as described in Gross (Gross, J. R. et al. (2002) *Diabetes*, 51:2227-32) and within the C57BL/6J background described in Craven (Craven, P. A. et al. (2001) *Diabetes*, 50:2114-25). Following the first STZ injection (day 0), blood sugar levels were taken daily to determine the diabetic status of the mice. In an alternative protocol, diabetes was induced by injecting the mice with 50 mg/kg of STZ daily for 5 days, with blood glucose levels being analyzed every other day. Diabetic mice were treated with insulin as necessary to improve the health and lifespan.

To determine if periostin could prevent STZ-induced diabetes, recombinant periostin (BioVendor; RD172045100) was injected following STZ treatment in mice. STZ treated mice were intraperitoneal (IP) injected with recombinant periostin at varying concentrations from 10 mg/kg to 90 mg/kg of body weight following the STZ injections described above. Blood glucose levels were analyzed every other day. Periostin was determined to prevent STZ-induced diabetes if periostin-treated mice maintained normal blood glucose levels but their non-periostin treated littermate control mice became diabetic. Eleven of fifteen animals were able to maintain normal blood glucose levels when injected with STZ and periostin (FIG. 4). This experiment also suggested that the optimal dose of IP-injected periostin in mice appears to be between 30-70 mg/kg body weight. A preferred dose of IP-injected periostin in mice appears to be between 40-60 mg/kg body weight.

Example 4

Isolation of DNA Encoding Periostin Isoform PANC

Pancreatic tissue was flash frozen in liquid nitrogen and quickly ground with a frozen mortar and pestle. Before thawing the ground pancreatic tissue was mixed with 1 ml of TRIZOL Reagent (Invitrogen cat#15596-018). The RNA from the pancreatic tissue was then isolated following the manufacturer's instructions.

RNA samples were reverse transcribed using the RNA PCR Core Kit (Applied Biosystems cat#N808-0143) following the manufacturer's instructions. Both Oligo d(T)s and Random hexamer primers supplied in the kit were used to initiate reverse transcription (RT) reactions to create the cDNA.

The PCR reaction to amplify the carboxy terminus of periostin from the cDNA created above included the following reagents: 5 µl cDNAs, 50 nM forward PCR primer AAACTC-CTCTATCCAGCAGA (SEQ ID NO: 4), 50 nM reverse PCR primer AACGGCCTTCTCTTGATCGTCT (SEQ ID NO: 5), 500 nM dNTPs, 1 mM $MgCl_2$, 5 µl of 10× reaction buffer and 0.25 µl TAQ polymerase (Invitrogen cat#10342-020). The reaction was diluted to 50 µl. The conditions for running the PCR reaction were as follows: 25 cycles (60 s at 95° C., 60 s at 60° C., and 60 s at 72° C.). The reaction was then run on a 2% agarose gel and the prominent band observed at 462 by was cut from the gel using a clean scalpel. The DNA fragment was extracted from the gel using the QIAquick Gel Extraction kit (Qiagen cat#28706) and following the manufacturer's instructions. Following the gel extraction the DNA fragment was sequenced using both the forward and reverse PCR primers described above in 2 separate reactions. More specifically, 2 µM of primer was used to sequence 10 ng of PCR template using an Applied Biosystems 3730 DNA Analyzer at Stemcore (OHRI, Ottawa, ON).

Example 5

Safety of Injected Periostin

To determine if periostin could be safely administered, the recombinant protein (BioVendor; RD172045100) was injected to mice, once per week for 6 weeks starting at 8 weeks of age, via an intra peritoneal injection at 0, 2, 4 or 10 µg/kg of body weight. No visible tumors were detected by week 13. The blood glucose level of each mouse was monitored on a weekly basis. The average blood glucose level, in mM/L, for each group of mice (6 mice per group) is shown in Table 1, below. Standard deviations ranged from 0.31 to 2.06 mM/L.

TABLE 1

| Periostin | Week | | | | | | | | | | | | | |
|---|---|---|---|---|---|---|---|---|---|---|---|---|---|---|
| | 0 | 1 | 2 | 3 | 4 | 5 | 6 | 7 | 8 | 9 | 10 | 11 | 12 | 13 |
| 0 µg/kg | 8.08 | 8.90 | 9.40 | 8.07 | 8.93 | 7.80 | 8.72 | 8.40 | 8.05 | 7.27 | 6.73 | 7.08 | 6.65 | 7.38 |
| 2 µg/kg | 7.58 | 9.41 | 8.48 | 8.37 | 9.42 | 7.83 | 8.48 | 7.80 | 7.83 | 7.18 | 8.22 | 7.87 | 6.65 | 8.15 |
| 4 µg/kg | 6.30 | 8.47 | 8.00 | 7.72 | 7.93 | 6.78 | 8.98 | 7.47 | 7.02 | 8.03 | 7.52 | 7.68 | 7.17 | 6.55 |
| 10 µg/kg | 7.33 | 8.63 | 8.75 | 6.55 | 7.75 | 8.40 | 9.22 | 8.12 | 7.38 | 7.65 | 7.57 | 7.58 | 7.32 | 7.40 |

Example 6

Stellate Cells Express Periostin and Mediate Pancreatic Regeneration

To determine if stellate cells are the cellular source of periostin during pancreas regeneration, a highly purified population of periostin expressing cells was isolated from the adult pancreas. The purified population of periostin expressing cells was isolated by (1) observing that, in the regenerating pancreas, periostin was expressed in cells that co-expressed Vimentin and Stem Cell Antigen-1 (Sca1/Ly6A), and (2) using standard fluorescence activated cell sorting (FACS) protocols to isolate live cells expressing Sca1 (using fluorochrome-conjugated Sca1-specific antibodies; eBioscience 17-5981) from the resting pancreas. Standard FACS protocols were used to identify $CD31^-$ cells (using fluorochrome-conjugated CD31-specific antibodies; eBioscience 12-0112) to remove endothelial cells that also express Sca1.

The FACS-purified $Sca1^+/CD31^-$ cells were cultured and expanded in RPMI medium with 10% fetal calf serum. In culture, the $Sca1^+/CD31^-$ cells exhibited morphology and markers of pancreatic stellate cells ($Vimentin^+$, smooth muscle $actin^+$, $Desmin^+$, $Nestin^+$, $GFAP^+$, $Cytokeratin-7^-$, $E-Cadherin^-$, $amylase^-$ and $insulin^-$). Expression of heterozygous periostin-LacZ allele was determined by fluorescein digalactoside (FDG) staining and flow cytometry to be limited to $Sca1^+$ cells. Additionally, standard quantitative PCR protocols identified the cultured $Sca1^+/CD31^-$ cells as expressed periostin mRNA. These results indicate that pancreatic stellate cells are the cellular source of periostin during pancreas regeneration.

Example 7

Mesenchymal Stellate Cells Induce Pancreatic Regeneration $Sca1^+$ stellate cells, infected with lentiviral-GFP, were directly injected into the pancreas of recipient mice (1E4 cells/mouse). Wild-type stellate cells were observed to infiltrate the recipient pancreas and induce tubular complex formation and generation of Ngn3 progenitor cells as well as Pdx1 expressing islet cells. At two weeks post injection, staining with anti-GFP antibody (Invitrogen A21311) under standard protocols revealed donor cells scattered throughout the endocrine tissue. Areas containing GFP-expressing donor cells also contained tubular complexes that expressed Ngn3. Tubular complexes did not contain donor cells as neither Cytokeratin-7 nor Pdx-1 co-localized with GFP.

Figure 6:
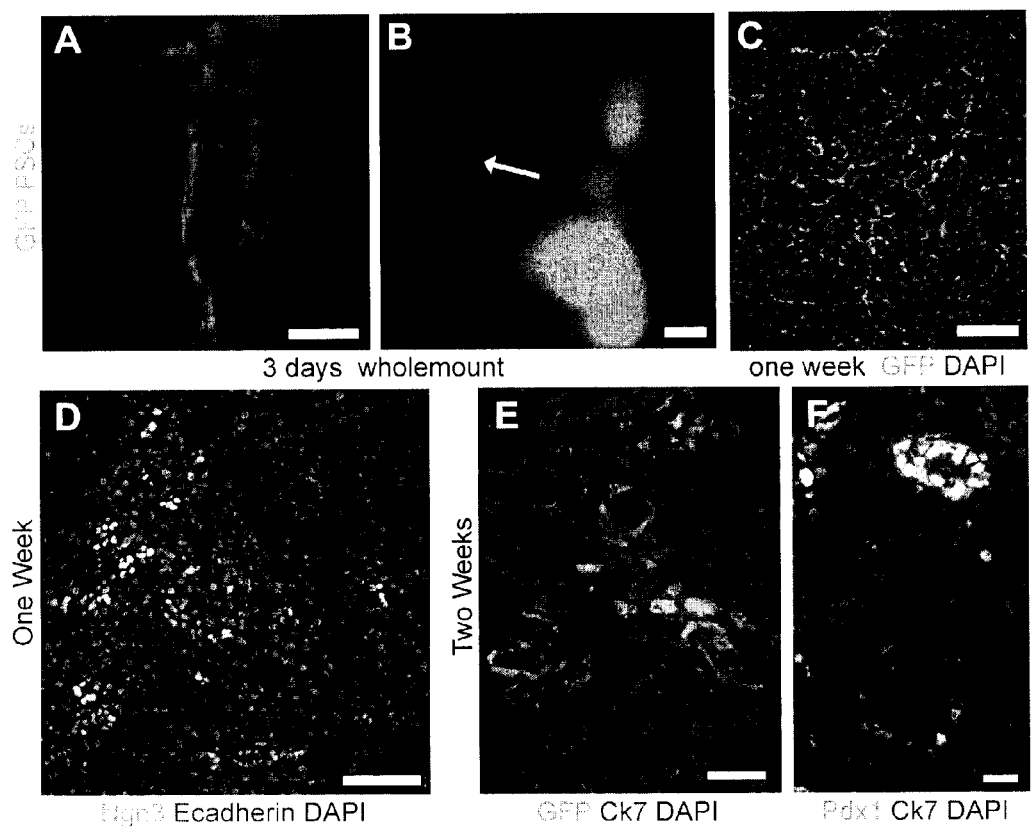
FIG. 6 shows histology of the pancreas with transplanted pancreatic stellate cells.
Figure 7:
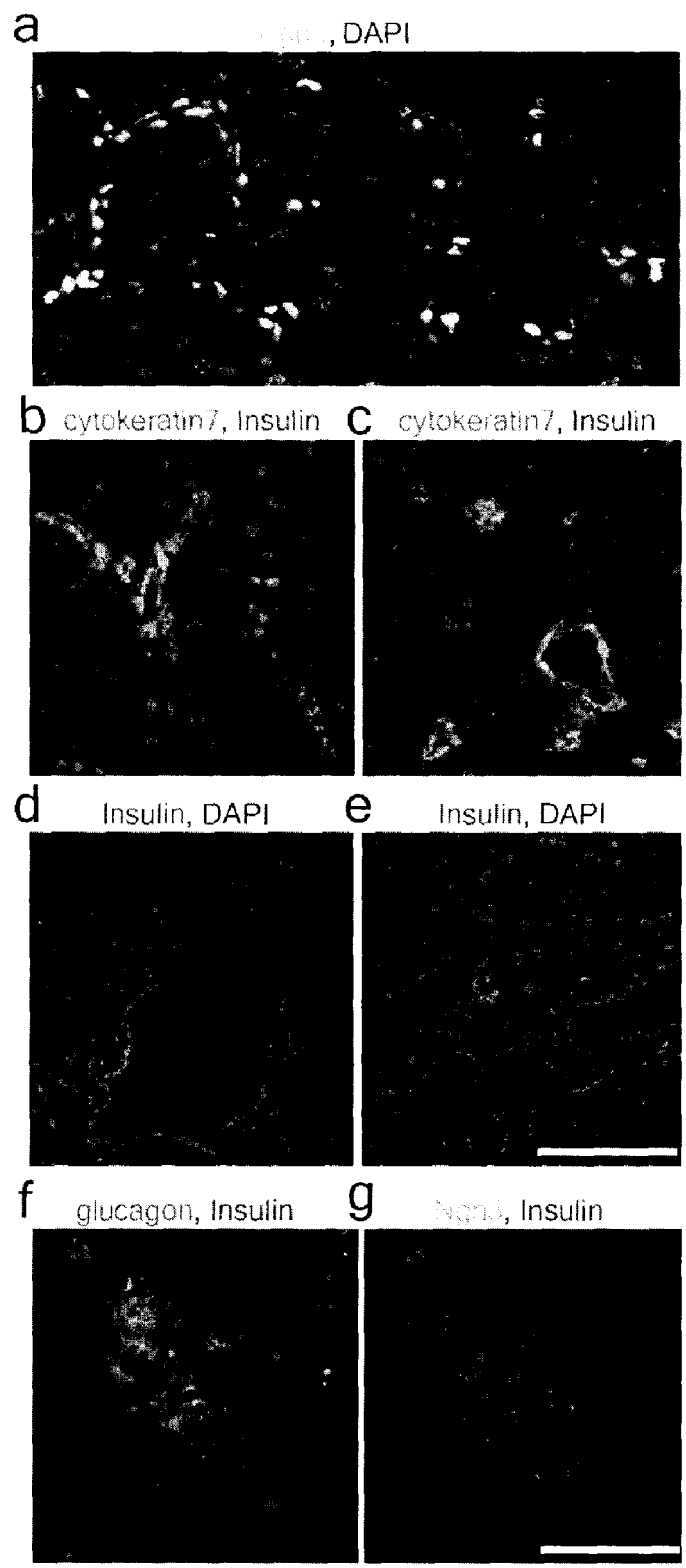
FIG. 7 illustrates the effects of directly injected periostin on pancreatic regeneration and insulin expression. 7A-G illustrate: (A) One week following injection of periostin, Ngn3+ cells are found near the injection track; (B) insulin expression is observed in Cytokeratin-7+ tubular complex structures; (C) no insulin expression was detected following saline injection; (D and E) four weeks following injection, insulin expression is observed within and around ductal structures; (F) the insulin+ clusters contain cells that express glucagon; (G) the insulin+ clusters contain cells that express Ngn3.

FIG. 6 shows histology of the pancreas with transplanted pancreatic stellate cells. FIGS. 6A and 6C show infiltration of GFP-expressing wild type donor cells 3 days and one week after injection, respectively. FIG. 6A is a magnified view of the area indicated by the arrow in FIG. 6B. The scale bar for FIG. 6A is 500 µm, while the scale bar for FIG. 6B is 1 mm. FIGS. 6D-F show that pancreas injected with wild type cells exhibited: (D) formation of tubular complexes expressing E-Cadherin and Ngn3; (E) GFP-expressing cells surrounding Cytokeratin-7 ductal structures; and (F) GFP-expressing cells did not express Pdx1.

Example 8

Periostin-Induced Pancreatic Regeneration and Insulin Expression

To determine if periostin induced pancreatic regeneration in STZ-treated diabetic mice, STZ was injected daily for five days following the protocol described above. After one week, recombinant periostin was directly injected into the pancreas (5 mg/kg of body weight) following the protocol described above. One week following the periostin injection, tubular complex formation and generation of Ngn3-expressing progenitor cells, together with insulin expression within cells in ducts, was seen. At four weeks following the periostin injection, insulin expression was found using standard histology techniques in clusters within and surrounding ducts that contained both insulin- and glucagon-positive cells which still expressed Ngn3, suggesting that the clusters are immature islets.

FIGS. 7A-G illustrate: (A) One week following injection of periostin, Ngn3+ cells are found near the injection track; (B) insulin expression is observed in Cytokeratin-7+ tubular complex structures; (C) no insulin expression was detected following saline injection; (D and E) four weeks following injection, insulin expression is observed within and around ductal structures; (F) the insulin+ clusters contain cells that express glucagon; (G) the insulin+ clusters contain cells that express Ngn3.

In the preceding description, for purposes of explanation, numerous details are set forth in order to provide a thorough understanding of the embodiments of the invention. However, it will be apparent to one skilled in the art that these specific details are not required in order to practice the invention. The above-described embodiments of the invention are intended to be examples only. Alterations, modifications and variations can be effected to the particular embodiments by those of skill in the art without departing from the scope of the invention, which is defined solely by the claims appended hereto.

The invention claimed is:

1. A method for regenerating pancreatic tissue comprising administering an effective amount of periostin to a subject in need of pancreatic regeneration.

2. The method according to claim 1, wherein the periostin is a recombinant periostin having the amino acid sequence set forth in the SEQ ID NO: 10.

3. The method according to claim 1, wherein the regenerated pancreatic tissue comprises β-cells.

4. The method according to claim 1, for use in the treatment of insulin dependent diabetes mellitus.

5. The method according to claim 1, wherein the administration is by injection.

6. The method according to claim 5, wherein the injection is into the intraperitoneal space, into circulation, or directly into the pancreas.

7. The method according to claim 1, wherein the administration is a surgical insertion of a gel or matrix comprising the periostin.

8. The method according to claim 1 wherein the regenerated tissue releases insulin.

9. A method of treating diabetes by administering an effective amount of periostin, to a patient in need of pancreatic regeneration.

10. The method according to claim 9, wherein the administration is by surgical insertion of a gel or matrix comprising the periostin.

11. A method of treating diabetes by administering an effective amount of the recombinant periostin of claim 2 to a patient in need of pancreatic regeneration.

12. The method according to claim 9 or claim 11, wherein the regenerated pancreatic tissue comprises β-cells.

13. The method according to claim 9 or claim 11, wherein the diabetes is insulin dependent diabetes mellitus.

14. The method according to claim 9 or claim 11, wherein the administration is by injection.

15. The method according to claim 14, wherein the administration is by injection into the intraperitoneal space, into circulation, or directly into the pancreas.

16. The method according to claim 9 or claim 11, wherein the regenerated tissue releases insulin.

17. The method according to claim 11, wherein the administration is by surgical insertion of a gel or matrix comprising the recombinant periostin of claim 2.

* * * * *

SEQUENCE LISTING

<160> NUMBER OF SEQ ID NOS: 10

<210> SEQ ID NO 1
<211> LENGTH: 463
<212> TYPE: DNA
<213> ORGANISM: Mus musculus

<400> SEQUENCE: 1

| aaactcctct | atccagcaga | tattccagtt | ggaaatgatc | agctcttgga | attactgaac | 60 |
| aaactgataa | aatacatcca | aatcaagttt | gttcgtggca | gcaccttcaa | agaaatcccc | 120 |
| atgactgtct | atagacctgc | aatgacgaag | atccaaattg | aaggtgatcc | cgacttcagg | 180 |
| ctgattaaag | aaggcgaaac | ggtgacgaa | gtgatccacg | gagagccagt | cattaaaaag | 240 |
| tacaccaaaa | tcatagatgg | agttcctgtt | gaaataactg | aaaaacagac | tcgggaagaa | 300 |
| cgaatcatta | caggtcctga | gataaaatat | accaggatt | ccacaggagg | tggagaaaca | 360 |
| ggagagacct | tgcagaaatt | cttgcaaaaa | gacacacctg | caaagaagat | accagccaac | 420 |
| aaaagggttc | aagggcctag | aagacgatca | agagaaggcc | gtt | | 463 |

<210> SEQ ID NO 2
<211> LENGTH: 783
<212> TYPE: PRT
<213> ORGANISM: Mus musculus

<400> SEQUENCE: 2

Met Val Pro Leu Leu Pro Leu Tyr Ala Leu Leu Leu Leu Phe Leu Cys
1               5                   10                  15

Asp Ile Asn Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Tyr Phe Ser Ser Cys Lys Asn
    50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
        115                 120                 125

Glu Gly Lys Gly Ser Tyr Thr Tyr Phe Ala Pro Ser Asn Glu Ala Trp
    130                 135                 140

Glu Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
                165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
        195                 200                 205

Asn Cys Ala Arg Val Ile His Gly Asn Gln Ile Ala Thr Asn Gly Val
    210                 215                 220

Val His Val Ile Asp Arg Val Leu Thr Gln Ile Gly Thr Ser Ile Gln
225                 230                 235                 240

```
Asp Phe Leu Glu Ala Glu Asp Leu Ser Ser Phe Arg Ala Ala
            245                 250                 255

Ile Thr Ser Asp Leu Leu Glu Ser Leu Gly Arg Asp Gly His Phe Thr
            260                 265                 270

Leu Phe Ala Pro Thr Asn Glu Ala Phe Glu Lys Leu Pro Arg Gly Val
            275                 280                 285

Leu Glu Arg Ile Met Gly Asp Lys Val Ala Ser Glu Ala Leu Met Lys
            290                 295                 300

Tyr His Ile Leu Asn Thr Leu Gln Cys Ser Glu Ala Ile Thr Gly Gly
305                 310                 315                 320

Ala Val Phe Glu Thr Met Gly Asn Thr Ile Glu Ile Gly Cys Glu
                325                 330                 335

Gly Asp Ser Ile Ser Ile Asn Gly Ile Lys Met Val Asn Lys Lys Asp
            340                 345                 350

Ile Val Thr Lys Asn Gly Val Ile His Leu Ile Asp Glu Val Leu Ile
            355                 360                 365

Pro Asp Ser Ala Lys Gln Val Ile Glu Leu Ala Gly Lys Gln Gln Thr
            370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
            405                 410                 415

Asp Asp Thr Leu Ser Met Asp Gln Arg Leu Leu Lys Leu Ile Leu Gln
            420                 425                 430

Asn His Ile Leu Lys Val Lys Val Gly Leu Ser Asp Leu Tyr Asn Gly
            435                 440                 445

Gln Ile Leu Glu Thr Ile Gly Gly Lys Gln Leu Arg Val Phe Val Tyr
            450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
            485                 490                 495

Ala Glu Lys Ser Leu His Asp Lys Leu Arg Gln Asp Lys Arg Phe Ser
            500                 505                 510

Ile Phe Leu Ser Leu Leu Glu Ala Ala Asp Leu Lys Asp Leu Leu Thr
            515                 520                 525

Gln Pro Gly Asp Trp Thr Leu Phe Ala Pro Thr Asn Asp Ala Phe Lys
            530                 535                 540

Gly Met Thr Ser Glu Glu Arg Glu Leu Leu Ile Gly Asp Lys Asn Ala
545                 550                 555                 560

Leu Gln Asn Ile Ile Leu Tyr His Leu Thr Pro Gly Val Tyr Ile Gly
            565                 570                 575

Lys Gly Phe Glu Pro Gly Val Thr Asn Ile Leu Lys Thr Thr Gln Gly
            580                 585                 590

Ser Lys Ile Tyr Leu Lys Gly Val Asn Glu Thr Leu Leu Val Asn Glu
            595                 600                 605

Leu Lys Ser Lys Glu Ser Asp Ile Met Thr Thr Asn Gly Val Ile His
            610                 615                 620

Val Val Asp Lys Leu Leu Tyr Pro Ala Asp Ile Pro Val Gly Asn Asp
625                 630                 635                 640

Gln Leu Leu Glu Leu Leu Asn Lys Leu Ile Lys Tyr Ile Gln Ile Lys
            645                 650                 655

Phe Val Arg Gly Ser Thr Phe Lys Glu Ile Pro Met Thr Val Tyr Arg
```

```
                    660             665             670
Pro Ala Met Thr Lys Ile Gln Ile Glu Gly Asp Pro Asp Phe Arg Leu
            675                 680                 685

Ile Lys Glu Gly Glu Thr Val Thr Glu Val Ile His Gly Glu Pro Val
            690                 695                 700

Ile Lys Lys Tyr Thr Lys Ile Ile Asp Gly Val Pro Val Glu Ile Thr
705                 710                 715                 720

Glu Lys Gln Thr Arg Glu Arg Ile Ile Thr Gly Pro Glu Ile Lys
                725                 730                 735

Tyr Thr Arg Ile Ser Thr Gly Gly Glu Thr Gly Glu Thr Leu Gln
                740                 745                 750

Lys Phe Leu Gln Lys Asp Thr Pro Ala Lys Lys Ile Pro Ala Asn Lys
                755                 760                 765

Arg Val Gln Gly Pro Arg Arg Arg Ser Arg Glu Gly Arg Ser Gln
                770                 775                 780

<210> SEQ ID NO 3
<211> LENGTH: 2352
<212> TYPE: DNA
<213> ORGANISM: Mus musculus

<400> SEQUENCE: 3
atggttcctc tcctgccctt atatgctctg ctgctgctgt tcctgtgtga tattaaccct    60
gcaaatgcca acagttacta tgacaaggtc ctggctcaca gccgcatcag ggtcgggat    120 cagggcccaa acgtctgtgc cctccagcaa attctgggca ccaaaaagaa atacttcagc    180
tcctgtaaga actggtatca aggtgctatc tgcgggaaga aaaccactgt gctatatgaa    240
tgctgccctg ctatatgag aatggaaggg atgaaaggct gccccgcagt gatgcctatt    300
gaccatgttt atggcacgct gggcattgtg ggagccacta ccactcagca ctactccgat    360
gtctcgaagc tgagagaaga gattgaagga aagggtcat acacgtactt cgcgccgagt    420
aacgaggctt gggagaacct ggattctgac attcgcagag actggagaa caatgtcaat    480 gttgagctac tgaatgcctt acacagccac atggttaata agagaatgtt aaccaaggac    540
ctgaaacacg gcatggttat tccttcaatg tacaacaatc tggggctttt tattaaccat    600
tatcccaatg gggttgtcac tgtgaactgt gctcgagtca tccatgggaa ccagattgcc    660
acaaatggtg tcgtccatgt cattgaccgt gtcctgacac aaattggtac ctccatccaa    720
gacttccttg aagcagaaga cgacctttca tcatttagag cagccgccat cacctctgac    780
ctcttggagt cccttggaag agatggtcac ttcacgctct ttgctcccac caatgaagct    840
ttcgagaaac tgccacgagg tgtcctagaa aggatcatgg agacaaagt ggcttctgaa    900 gctctcatga agtaccacat cctaaatacc ctccagtgct ctgaggccat cactggagga    960
gccgtgtttg agaccatgga aggaaacact attgagatag ggtgcgaagg ggacagtatc    1020
tccattaacg gaatcaagat ggtgaacaag aaagacattg tgactaagaa tggtgtcatc    1080
cacctgattg atgaagtcct cattcctgat tctgccaaac aagttattga gctggctgga    1140
aaacagcaaa ccactttcac cgacctggta gcccaattag gcttggcatc ctctctgaag    1200
ccagatggag agtacacctt attagcacct gtgaacaatg cgttctctga tgacactctg    1260
agcatggacc aacgccttct taagctaatt ctgcaaaatc acatattgaa agtaaaagtt    1320
ggccttagcg acctctacaa tggacagata ctggaaacca ttggaggcaa acaactccga    1380
gtctttgtgt atcggacggc tatctgcata gaaaactcat gcatggtgag aggaagcaag    1440
cagggaagga atggtgccat tcacatattc cgagaaatca tccaaccagc agagaaatcc    1500
```

```
ctgcacgaca agctgcggca agacaagcgc tttagcatct tcctcagcct ccttgaagct    1560
gcagatttga aagatctcct gacacagccc ggagattgga ccttgtttgc accaaccaat    1620
gatgccttca agggaatgac tagcgaagaa agggagcttc tgattgggga taaaaatgct    1680
ctccaaaaca tcattcttta tcacctgacc ccaggggttt atattggaaa gggattcgaa    1740
cccggagtca ctaatatcct gaagaccaca cagggaagca aaatctatct gaaaggagta    1800
aacgaaacgc ttctagtgaa tgagttgaag tccaaagaat ctgacatcat gacgacaaat    1860
ggtgtcatcc acgtcgtgga caaactcctc tatccagcag atattccagt tggaaatgat    1920
cagctcttgg aattactgaa caaactgata aaatacatcc aaatcaagtt tgttcgtggc    1980
agcaccttca agaaatccc catgactgtc tatagacctg caatgacgaa gatccaaatt    2040
gaaggtgatc ccgacttcag gctgattaaa gaaggcgaaa cggtgacaga agtgatccac    2100
ggagagccag tcattaaaaa gtacaccaaa atcatagatg gagttcctgt tgaaataact    2160
gaaaaacaga ctcgggaaga acgaatcatt acaggtcctg agataaaata taccaggatt    2220
tccacaggag gtggagaaac aggagagacc ttgcagaaat tcttgcaaaa agacacacct    2280
gcaaagaaga taccagccaa caaagggtt caagggccta agacgatc aagagaaggc       2340 cgttctcagt ga                                                       2352
```

```
<210> SEQ ID NO 4
<211> LENGTH: 20
<212> TYPE: DNA
<213> ORGANISM: Artificial
<220> FEATURE:
<223> OTHER INFORMATION: forward primer, for amplying periostin eDNA

<400> SEQUENCE: 4
aaactcctct atccagcaga                                                  20

<210> SEQ ID NO 5
<211> LENGTH: 22
<212> TYPE: DNA
<213> ORGANISM: Artificial
<220> FEATURE:
<223> OTHER INFORMATION: reverse primer, for amplifying periostin eDNA

<400> SEQUENCE: 5
aacggccttc tcttgatcgt ct                                               22

<210> SEQ ID NO 6
<211> LENGTH: 636
<212> TYPE: DNA
<213> ORGANISM: Mus musculus
<220> FEATURE:
<223> OTHER INFORMATION: periostin isoform #1 (PN1)

<400> SEQUENCE: 6
aaactcctct atccagcaga tattccagtt ggaaatgatc agctcttgga attactgaac      60
aaactgataa aatacatcca aatcaagttt gttcgtggca gcaccttcaa agaaatcccc     120
atgactgtct atacaactaa aattataacc aaagtcgtgg aaccaaaaat taaagtcatt     180
caaggcagtc ttcagcctat tatcaaaacg gaaggacctg caatgacgaa gatccaaatt     240
gaaggtgatc ccgacttcag gctgattaaa gaaggcgaaa cggtgacaga agtgatccac     300
ggagagccag tcattaaaaa gtacaccaaa atcatagatg gagttcctgt tgaaataact     360
gaaaaacaga ctcgggaaga acgaatcatt acaggtcctg agataaaata taccaggatt     420
tccacaggag gtggagaaac aggagagacc ttgcagaaat tcttgcaaaa agaggtctcc     480
```

| aaggtcacaa agttcattga aggtggcgat ggtcacttat ttgaagatga ggagattaaa | 540 |
| agactgcttc agggagacac acctgcaaag aagataccag ccaacaaaag ggttcaaggg | 600 |
| cctagaagac gatcaagaga aggccgttct cagtga | 636 |

<210> SEQ ID NO 7
<211> LENGTH: 555
<212> TYPE: DNA
<213> ORGANISM: Mus musculus
<220> FEATURE:
<223> OTHER INFORMATION: periostin isoform #2 (PN2)

<400> SEQUENCE: 7

| aaactcctct atccagcaga tattccagtt ggaaatgatc agctcttgga attactgaac | 60 |
| aaactgataa aatacatcca aatcaagttt gttcgtggca gcaccttcaa agaaatcccc | 120 |
| atgactgtct atagacctgc aatgacgaag atccaaattg aaggtgatcc cgacttcagg | 180 |
| ctgattaaag aaggcgaaac ggtgacagaa gtgatccacg agagccagt cattaaaaag | 240 |
| tacaccaaaa tcatagatgg agttcctgtt gaaataactg aaaaacagac tcgggaagaa | 300 |
| cgaatcatta caggtcctga gataaaatat accaggattt ccacaggagg tggagaaaca | 360 |
| ggagagacct tgcagaaatt cttgcaaaaa gaggtctcca aggtcacaaa gttcattgaa | 420 |
| ggtggcgatg gtcacttatt tgaagatgag gagattaaaa gactgcttca gggagacaca | 480 |
| cctgcaaaga agataccagc caacaaaagg gttcaagggc tagaagacg atcaagagaa | 540 |
| ggccgttctc agtga | 555 |

<210> SEQ ID NO 8
<211> LENGTH: 552
<212> TYPE: DNA
<213> ORGANISM: Mus musculus
<220> FEATURE:
<223> OTHER INFORMATION: periostin isoform #3 (PN3)

<400> SEQUENCE: 8

| aaactcctct atccagcaga tattccagtt ggaaatgatc agctcttgga attactgaac | 60 |
| aaactgataa aatacatcca aatcaagttt gttcgtggca gcaccttcaa agaaatcccc | 120 |
| atgactgtct atacaactaa aattataacc aaagtcgtgg aaccaaaaat taaagtcatt | 180 |
| caaggcagtc ttcagcctat tatcaaaacg gaaggacctg caatgacgaa gatccaaatt | 240 |
| gaaggtgatc ccgacttcag gctgattaaa gaaggcgaaa cggtgacaga agtgatccac | 300 |
| ggagagccag tcattaaaaa gtacaccaaa atcatagatg gagttcctgt tgaaataact | 360 |
| gaaaaacaga ctcgggaaga acgaatcatt acaggtcctg agataaaata taccaggatt | 420 |
| tccacaggag gtggagaaac aggagagacc ttgcagaaat tcttgcaaaa agacacacct | 480 |
| gcaaagaaga taccagccaa caaagggtt caagggccta agacgatc aagagaaggc | 540 |
| cgttctcagt ga | 552 |

<210> SEQ ID NO 9
<211> LENGTH: 474
<212> TYPE: DNA
<213> ORGANISM: Mus musculus
<220> FEATURE:
<223> OTHER INFORMATION: periostin isoform #4 (PN4)

<400> SEQUENCE: 9

| aaactcctct atccagcaga tattccagtt ggaaatgatc agctcttgga attactgaac | 60 |

```
aaactgataa atacatcca aatcaagttt gttcgtggca gcaccttcaa agaaatcccc    120
atgactgtct atacaactaa aattataacc aaagtcgtgg aaccaaaaat taaagtcatt    180
caaggcagtc ttcagcctat tatcaaaacg aaggacctg caatgacgaa gatccaaatt    240
gaaggtgatc ccgacttcag gctgattaaa gaaggcgaaa cggtgacaga agtgatccac    300
ggagagccag tcattaaaaa gtacaccaaa atcatagatg gagttcctgt tgaaataact    360
gaaaaacaga ctcgggaaga acgaatcatt acagacacac ctgcaaagaa gataccagcc    420
aacaaaaggg ttcaagggcc tagaagacga tcaagagaag gccgttctca gtga          474
```

<210> SEQ ID NO 10
<211> LENGTH: 671
<212> TYPE: PRT
<213> ORGANISM: Artificial Sequence
<220> FEATURE:
<223> OTHER INFORMATION: recombinant human periostin

<400> SEQUENCE: 10

```
Met Gly His His His His His Asx His Asx His Ser Ser Gly His
1               5                  10                  15

Ile Glu Gly Arg His Met Arg Asn Asn His Tyr Asp Lys Ile Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Lys Tyr Phe Ser Thr Cys Lys Asn
    50                  55                  60

Trp Tyr Lys Lys Ser Ile Cys Gly Gln Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Leu Pro Ile Asp His Val Tyr Gly Thr Leu Gly Ile Val Gly Ala
            100                 105                 110

Thr Thr Thr Gln Arg Tyr Ser Asp Ala Ser Lys Leu Arg Glu Glu Ile
        115                 120                 125

Glu Gly Lys Gly Ser Phe Thr Tyr Phe Ala Pro Ser Asn Glu Ala Trp
    130                 135                 140

Asp Asn Leu Asp Ser Asp Ile Arg Arg Gly Leu Glu Ser Asn Val Asn
145                 150                 155                 160

Val Glu Leu Leu Asn Ala Leu His Ser His Met Ile Asn Lys Arg Asn
                165                 170                 175

Leu Thr Lys Asp Leu Lys Asn Gly Met Ile Ile Pro Ser Met Tyr Asn
            180                 185                 190

Asn Leu Gly Leu Phe Ile Asn His Tyr Pro Asn Gly Val Val Thr Val
        195                 200                 205

Asn Cys Ala Arg Ile Ile His Gly Asn Gln Ile Ala Thr Asn Gly Val
    210                 215                 220

Val His Val Ile Asp Arg Val Leu Thr Gln Ile Gly Thr Ser Ile Gln
225                 230                 235                 240

Asp Phe Ile Glu Ala Glu Asp Asp Leu Ser Ser Phe Arg Ala Ala Ala
                245                 250                 255

Ile Thr Ser Asp Ile Leu Glu Ala Leu Gly Arg Asp Gly His Phe Thr
            260                 265                 270

Leu Phe Ala Pro Thr Asn Glu Ala Phe Glu Lys Leu Pro Arg Gly Val
        275                 280                 285
```

```
Leu Glu Arg Phe Met Gly Asp Lys Val Ala Ser Glu Ala Leu Met Lys
    290                 295                 300

Tyr His Ile Leu Asn Thr Leu Gln Cys Ser Glu Ser Ile Met Gly Gly
305                 310                 315                 320

Ala Val Phe Glu Thr Leu Glu Gly Asn Thr Ile Glu Ile Gly Cys Asp
                325                 330                 335

Gly Asp Ser Ile Thr Val Asn Gly Ile Lys Met Val Asn Lys Lys Asp
            340                 345                 350

Ile Val Thr Asn Asn Gly Val Ile His Leu Ile Asp Gln Val Leu Ile
        355                 360                 365

Pro Asp Ser Ala Lys Gln Val Ile Glu Leu Ala Gly Lys Gln Gln Thr
    370                 375                 380

Thr Phe Thr Asp Leu Val Ala Gln Leu Gly Leu Ala Ser Ala Leu Arg
385                 390                 395                 400

Pro Asp Gly Glu Tyr Thr Leu Leu Ala Pro Val Asn Asn Ala Phe Ser
                405                 410                 415

Asp Asp Thr Leu Ser Met Val Gln Arg Leu Leu Lys Leu Ile Leu Gln
            420                 425                 430

Asn His Ile Leu Lys Val Lys Val Gly Leu Asn Glu Leu Tyr Asn Gly
        435                 440                 445

Gln Ile Leu Glu Thr Ile Gly Gly Lys Gln Leu Arg Val Phe Val Tyr
    450                 455                 460

Arg Thr Ala Val Cys Ile Glu Asn Ser Cys Met Glu Lys Gly Ser Lys
465                 470                 475                 480

Gln Gly Arg Asn Gly Ala Ile His Ile Phe Arg Glu Ile Ile Lys Pro
                485                 490                 495

Ala Glu Lys Ser Leu His Glu Lys Leu Lys Gln Asp Lys Arg Phe Ser
            500                 505                 510

Thr Phe Leu Ser Leu Leu Glu Ala Ala Asp Leu Lys Glu Leu Leu Thr
        515                 520                 525

Gln Pro Gly Asp Trp Thr Leu Phe Val Pro Thr Asn Asp Ala Phe Lys
    530                 535                 540

Gly Met Thr Ser Glu Glu Lys Glu Ile Leu Ile Arg Asp Lys Asn Ala
545                 550                 555                 560

Leu Gln Asn Ile Ile Leu Tyr His Leu Thr Pro Gly Val Phe Ile Gly
                565                 570                 575

Lys Gly Phe Glu Pro Gly Val Thr Asn Ile Leu Lys Thr Thr Gln Gly
            580                 585                 590

Ser Lys Ile Phe Leu Lys Glu Val Asn Asp Thr Leu Leu Val Asn Glu
        595                 600                 605

Leu Lys Ser Lys Glu Ser Asp Ile Met Thr Thr Asn Gly Val Ile His
    610                 615                 620

Val Val Asp Lys Leu Leu Tyr Pro Ala Asp Thr Pro Val Gly Asn Asp
625                 630                 635                 640

Gln Leu Leu Glu Ile Leu Asn Lys Leu Ile Lys Tyr Ile Gln Ile Lys
                645                 650                 655

Phe Val Arg Gly Ser Thr Phe Lys Glu Ile Pro Val Thr Val Tyr
            660                 665                 670
```